US010702343B2

(12) United States Patent
Kozak et al.

(10) Patent No.: US 10,702,343 B2
(45) Date of Patent: Jul. 7, 2020

(54) MEDICAL INSTRUMENTATION INCLUDING A NAVIGATION SYSTEM (71) Applicant: Aesculap AG, Tuttlingen (DE)

(72) Inventors: Josef Kozak, Tuttlingen (DE); Jens Beger, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 337 days.

(21) Appl. No.: 15/679,306

(22) Filed: Aug. 17, 2017

(65) Prior Publication Data
US 2017/0360515 A1 Dec. 21, 2017

Related U.S. Application Data (63) Continuation of application No. PCT/EP2016/051582, filed on Jan. 26, 2016.

(30) Foreign Application Priority Data

Feb. 26, 2015 (DE) .................. 10 2015 102 768

(51) Int. Cl.
A61B 34/20 (2016.01)
A61B 17/70 (2006.01)
(Continued)

(52) U.S. Cl.
CPC .......... A61B 34/20 (2016.02); A61B 17/7083 (2013.01); A61B 90/30 (2016.02);
(Continued)

(58) Field of Classification Search
CPC ................ A61B 34/20; A61B 17/7083; A61B 2034/2055
See application file for complete search history.

(56) References Cited

U.S. PATENT DOCUMENTS 6,036,691 A 3/2000 Richardson
6,226,548 B1 5/2001 Foley et al.
(Continued)

FOREIGN PATENT DOCUMENTS

DE 10314882 10/2004
DE 102005026654 12/2006
(Continued)

OTHER PUBLICATIONS iPhone5; Apple Inc. Modified: Oct. 24, 2013. Accessed on Internet Archive, Sep. 15, 2019. (Year: 2013).*
(Continued)

Primary Examiner — David W Bates
(74) Attorney, Agent, or Firm — Lipsitz & McAllister, LLC (57) ABSTRACT The invention relates to a medical instrumentation, comprising a hand-held, integrated, medical navigation system which comprises an optical detection unit having a camera, a data processing unit and an optical display unit, the data processing unit being coupled to the detection unit and the display unit, it being possible for location and/or orientation data of a medical marking device which is detectable with the detection unit to be processed by the data processing unit and information relating thereto to be represented on the display unit, the instrumentation comprising an illumination unit with which light is emittable in the direction of the marking device detectable with the detection unit.

17 Claims, 7 Drawing Sheets (51) Int. Cl.
*A61B 90/00* (2016.01)
*A61B 90/30* (2016.01)
*A61B 34/10* (2016.01)
*A61B 17/88* (2006.01)

(52) U.S. Cl.
CPC .......... *A61B 90/39* (2016.02); *A61B 17/8863* (2013.01); *A61B 34/10* (2016.02); *A61B 90/37* (2016.02); *A61B 2034/108* (2016.02); *A61B 2034/2048* (2016.02); *A61B 2034/2055* (2016.02); *A61B 2034/2057* (2016.02); *A61B 2034/2074* (2016.02); *A61B 2090/061* (2016.02); *A61B 2090/3937* (2016.02); *A61B 2090/3983* (2016.02)

(56) References Cited

U.S. PATENT DOCUMENTS

| | | | |
|---|---|---|---|
| 7,561,733 | B2 | 7/2009 | Vilsmeier et al. |
| 7,763,030 | B2 | 7/2010 | Blau et al. |
| 7,809,184 | B2 | 10/2010 | Neubauer et al. |
| 7,835,778 | B2 | 11/2010 | Foley et al. |
| 7,862,568 | B2 | 1/2011 | Vilsmeier et al. |
| 7,922,731 | B2 * | 4/2011 | Schumacher ........ A61B 17/708 606/104 |
| 8,320,612 | B2 | 11/2012 | Knobel et al. |
| 8,534,848 | B2 | 9/2013 | Hauri et al. |
| 8,549,888 | B2 | 10/2013 | Isaacs |
| 9,314,281 | B2 | 4/2016 | Beger et al. |
| 9,414,859 | B2 | 8/2016 | Ballard et al. |
| 9,585,700 | B2 | 3/2017 | Wehrle et al. |
| 2003/0078565 | A1 | 4/2003 | Vilsmeier et al. |
| 2005/0262911 | A1 | 12/2005 | Dankowicz et al. |
| 2007/0160439 | A1 | 7/2007 | Vilsmeier et al. |
| 2009/0249851 | A1 | 10/2009 | Isaacs |
| 2010/0100081 | A1 * | 4/2010 | Tuma .................... A61B 34/20 606/1 |
| 2011/0286098 | A1 | 11/2011 | Hauri et al. |
| 2013/0066387 | A1 | 3/2013 | Beger et al. |
| 2014/0005531 | A1 * | 1/2014 | Taylor ..................... A61B 5/06 600/424 |
| 2014/0225999 | A1 | 8/2014 | Bracke et al. |
| 2014/0236159 | A1 * | 8/2014 | Haider ............... A61B 17/1626 606/88 |
| 2014/0316420 | A1 | 10/2014 | Ballard et al. |
| 2015/0133945 | A1 * | 5/2015 | Dushyant ............... A61B 90/57 606/102 |
| 2015/0182292 | A1 * | 7/2015 | Hladio ............... A61B 17/1746 606/87 |
| 2015/0305786 | A1 * | 10/2015 | Wehrle .................... A61B 90/98 606/86 A |
| 2017/0340367 | A1 * | 11/2017 | Beger ................ A61B 17/7002 |
| 2018/0049809 | A1 * | 2/2018 | Marti ..................... A61B 34/30 |

FOREIGN PATENT DOCUMENTS

| | | |
|---|---|---|
| DE | 102008022254 | 11/2009 |
| DE | 102010016448 | 10/2011 |
| DE | 202015100313 | 3/2015 |
| DE | 102014102398 | 8/2015 |
| DE | 102015102776 | 9/2016 |
| EP | 1281365 | 2/2003 |
| EP | 1413257 | 2/2005 |
| EP | 1657678 | 5/2006 |
| EP | 1719472 | 11/2006 |
| EP | 1523950 | 2/2009 |
| EP | 2910206 | 8/2015 |
| WO | 0159708 | 8/2001 |
| WO | 03020146 | 3/2003 |
| WO | 2009135838 | 11/2009 |
| WO | 2011020505 | 2/2011 |
| WO | 2013164770 | 11/2013 |
| WO | 2014088801 | 6/2014 |

OTHER PUBLICATIONS

Apple App Store; My Tools: My AR Ruler & Light, iDaily Corp. apps.apple.com/hk/app/mytools-my-ar-ruler-light/id557839389?l=en * note earliest review for the app is dated Nov. 17, 2012. Accessed Sep. 15, 2019. (Year: 2012).*

Top 10 Apps Like Mytools—My AR Ruler & Light. https://appfelstrudel.com/a/557839389/alternative-to-mytools-my-ar-ruler-light.html "First Release Sep. 28, 2012". Accessed Sep. 15, 2019. (Year: 2012).*

* cited by examiner

MEDICAL INSTRUMENTATION INCLUDING A NAVIGATION SYSTEM

CROSS-REFERENCE TO RELATED APPLICATIONS

This application is a continuation patent application of international application number PCT/EP2016/051582, filed on Jan. 26, 2016, and claims the benefit of German application number DE 10 2015 102 768.2, filed Feb. 26, 2015, which are incorporated herein by reference in their entirety and for all purposes.

FIELD OF THE INVENTION

The present invention relates to a medical instrumentation, comprising a medical navigation system.

BACKGROUND OF THE INVENTION

Such an instrumentation including navigation system is used in navigation-assisted surgical operations in order to assist the surgeon. Characteristic points marked by means of a medical marking device or landmarks on a patient can be recorded using the navigation system. It is also known to provide surgical instruments or implants with marking devices, the location and/or orientation of which are determined relative to the patient and especially to a reference marking arranged thereon.

Medical navigation systems prove to work well in practice. They do, however, have a space requirement that is not inconsiderable and entail costs that are not negligible.

An object underlying the present invention is to provide a medical instrumentation, comprising a medical navigation system which is of constructionally simple design and as far as possible can be manufactured cost-effectively.

SUMMARY OF THE INVENTION

In an aspect of the invention, a medical instrumentation comprises a hand-held, integrated, medical navigation system which comprises an optical detection unit having a camera, a data processing unit and an optical display unit, the data processing unit being coupled to the detection unit and the display unit. It is possible for location and/or orientation data of a medical marking device which is detectable with the detection unit to be processed by the data processing unit. Information relating thereto can be represented on the display unit. The instrumentation comprises an illumination unit with which light is emittable in the direction of the marking device detectable with the detection unit.

BRIEF DESCRIPTION OF THE DRAWINGS

The foregoing summary and the following description may be better understood in conjunction with the drawing figures. There are shown in.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical instrumentation, comprising a hand-held, integrated, medical navigation system which comprises an optical detection unit having a camera, a data processing unit and an optical display unit, the data processing unit being coupled to the detection unit and the display unit, it being possible for location and/or orientation data of a medical marking device which is detectable with the detection unit to be processed by the data processing unit and information relating thereto to be represented on the display unit, the instrumentation comprising an illumination unit with which light is emittable in the direction of the marking device detectable with the detection unit.

A hand-held, integrated, medical navigation system which can be employed in a user-friendly way is used in the instrumentation in accordance with the invention. As used herein, "integrated" may, in particular, be understood as meaning that the components of the navigation system—data processing unit, display unit, illumination unit—are accommodated in a common housing of the navigation system, and that the navigation system preferably has only one housing. For example, the surgeon can position the navigation system in any desired orientation in relation to the marking device to be detected, and so the navigation system proves to be not only easier to use than conventional, spatially fixed medical navigation systems, but also more versatile. By means of the illumination unit, light can be emitted in the direction of the marking device to be detected, and the light can be reflected by its marking elements and received by the camera of the detection unit. Owing to the illumination unit, it can be ensured that the marking device can be reliably detected in almost any relative orientation of the navigation system and the marking device. Furthermore, manufacturing costs for the instrumentation can be kept low by the integration of the components in a hand-held device.

The camera of the detection unit creates, in particular, an image or image sequences of the environment and the marking device arranged therein. Image processing algorithms enable the data processing unit to analyze the image or the images of the detection unit and to recognize the location and/or orientation of the marking device. By way of the marking device, it is, in particular, possible, as will be explained in more detail hereinbelow, for a reference coordinate system to be defined. Further characteristic points, reference points or landmarks with marking by additional marking devices can be recorded in the reference coordinate system. This does not require the navigation system to be spatially fixed relative to the marking devices.

It is particularly advantageous for the navigation system to be configured as smartphone or as tablet computer. A data processing program with which, in particular, with the aid of image processing algorithms, the images created by the camera are analyzed and the marking elements of the marking device recognized and tracked, can be executable in the data processing unit of the smartphone or tablet computer.

The navigation system advantageously comprises the illumination unit in order to achieve a constructionally simple design of the instrumentation.

It is expedient for the illumination unit to comprise at least one LED light source.

Visible light is preferably emittable by the illumination unit, for example, in a spectral range of from approximately 400 nm to approximately 800 nm or in part thereof.

The detection unit advantageously comprises precisely one camera in order to simplify the constructional design of the navigation system. The provision of a stereo camera is not necessary. The data processing unit can reliably track the marking device in space on the basis of the images of the one camera.

An image recordable with the camera is expediently representable on the display unit. In this way, additional information can be recorded beyond the tracking of the marking device. For example, the surgical procedure can be documented.

In particular, in connection with the last-mentioned advantageous embodiment, it is expedient for the navigation system to comprise a communication interface for transmitting data to an external receiving unit, in particular, images which are or were taken with the camera. As well as images of the camera, location and/or orientation data of the marking device, the data of characteristic points, reference points or anatomical landmarks can be transmitted, for example, for training or documentation purposes.

It is particularly advantageous for the navigation system to be freely movable in space and to be free of any mechanical coupling with a surgical instrument or an implant. As a result, the navigation system is more versatile in use, and the handling of the instrumentation is simplified for the operator.

The instrumentation can comprise at least one medical marking device which has a plurality of marking elements which are configured for retroflection of the light of the illumination unit. For example, the marking elements are optimized, in particular, for retroflection of visible light, for example, in the range of 400 nm to 800 nm.

It is expedient for the marking device to comprise four or more marking elements in order to increase the accuracy of the determination of the location and/or orientation of the marking device.

It proves advantageous for the marking device to comprise a holding element on which the marking elements are held, and contrast enhancement elements, a respective contrast enhancement element being associated with the marking elements in order to increase the contrast between the marking elements and the holding element.

For example, the contrast elements are configured as ring surrounding the respective marking element and having a reflectivity for the light emitted by the illumination unit, which is lower than the reflectivity of the marking elements. During the illumination, the marking elements reflect the light emitted by the illumination unit to a greater extent than the contrast enhancement elements. In the images of the camera, the image components of the marking elements can thereby be detected better by the data processing unit and the location and/or orientation of the marking device determined more accurately.

The marking device advantageously comprises hood-shaped protective elements which are associated with a respective marking element and which are transparent for the light emitted by the illumination unit. The protective elements have, for example, a spherical cap-shaped configuration and are optically transparent for visible light. The marking elements are protected against soiling, for example, by blood, by the protective elements.

In an advantageous embodiment, it is expedient for the instrumentation to comprise two or more marking devices, and for a space vector between reference points referenced by the marking devices to be determinable with the data processing unit, with one of the marking devices being usable as reference marking device for defining the reference coordinate system. In the reference coordinate system, which is defined by way of one marking device, the location and the orientation of the further marking device can be determined. Reference points referenced by the marking devices can thereby be connected via a space vector. This is possible independently of the position of the navigation system relative to the marking devices. It is thereby made possible for the surgeon to freely position the navigation system in order that he will have as good a view of the operating site and the marking devices as possible.

Advantageously, the marking devices are simultaneously detectable with the detection unit, and the space vector is determinable with the data processing unit on the basis of an, and, in particular, only one image of the camera.

It is expedient for the navigation system to comprise a sensor unit for providing a signal relating to the inclination of the navigation system in at least one direction in space of an absolute reference system, and for the orientation of the space vector to be determinable with the data processing unit in the absolute reference system. It is thereby made possible for location and orientation data to be transformed from the reference coordinate system of the marking device into the absolute reference system and vice versa. This allows, for example, axes and planes with anatomical landmarks to be determined without a priori knowledge of the position of the patient in the absolute reference system.

For example, on the basis of the orientations of a plurality of two or more space vectors, an inclination of a plane defined by these, for example, of the pelvic inlet plane, relative to a reference plane, in particular, a horizontal plane, can be determined in the absolute reference system.

In an advantageous embodiment, the instrumentation comprises two or more reference elements to be referenced, and the marking devices are preferably adapted for selective coupling to the reference elements, and the relative position of the reference elements is determinable by means of the data processing unit in the reference coordinate system. A respective marking device can be brought into a spatially defined position in relation to a reference element. The location and orientation of the reference element can thereby be determined in the reference coordinate system. Owing to a marking device remaining at one of the reference elements, and further reference elements to be referenced being marked with the further marking device, the relative position of the reference elements can be determined, for example, in the form of an open or closed polygonal line.

It may be provided that the marking elements are adapted for indirect or direct coupling to the reference elements.

The reference elements are, for example, bone screws or comprise bone screws, and the marking devices, preferably with extension elements, in particular, extension tubes, can be adapted for coupling, preferably percutaneously, to the bone screws. This allows the relative positions of the bone screws to be preferably percutaneously determined.

It is advantageous for the instrumentation to comprise a connecting element for connecting the reference elements, and for the geometry of the connecting element to be determinable by the data processing unit in order to connect the reference elements, preferably for an indication relating to the connecting element to be providable on the display unit. If the relative positions of the reference elements are known, the data processing unit can calculate what kind of a connecting element is required for connecting the reference elements to one another. An indication relating to this for selection or formation of a suitable connecting element can be represented on the display unit.

Expediently, the connecting element is adapted for coupling to one of the marking devices, and the position of the connecting element relative to the reference elements is preferably determinable by the data processing unit and indications are providable for a user on the display unit for guiding the connecting element. The user can be given instructions for connecting the reference elements to the connecting element via the navigation system and its display unit. For this purpose, the connecting element is adapted to be coupled or is coupled to a marking device, for example, the marking device is fixed to an implantation tool of the connecting element, as is the connecting element. By tracking the connecting element in the reference coordinate system, the connecting of the reference elements to one another is considerably simplified for the surgeon. This allows, in particular, simple percutaneous connection of the reference elements to one another.

The connecting element may, for example, be a rod, and the marking device is, as mentioned above, fixed or fixable to an insertion or implantation tool for guiding the rod.

Figure 1:
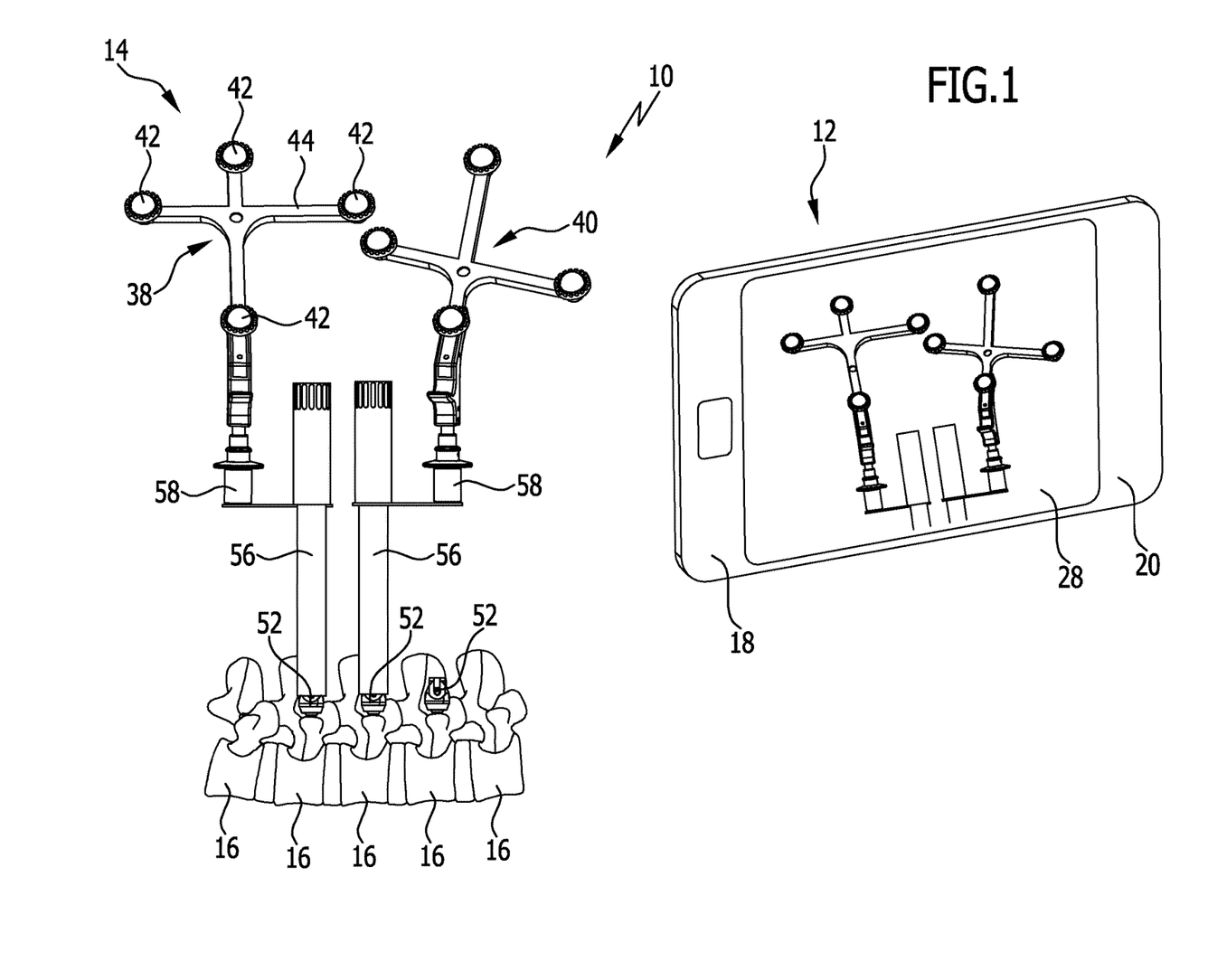
FIG. 1: a schematic illustration of an advantageous embodiment of an instrumentation in accordance with the invention, comprising a hand-held, integrated navigation system and a surgical fixation system.

FIG. 1 shows a schematic perspective illustration of an advantageous embodiment, denoted by reference numeral 10, of a medical instrumentation in accordance with the invention. The instrumentation 10 comprises a medical navigation system 12 and a surgical fixation system 14, which is shown only partially in FIG. 1. FIG. 1 also shows a plurality of vertebrae 16 to be stabilized relative to one another.

Figure 2:
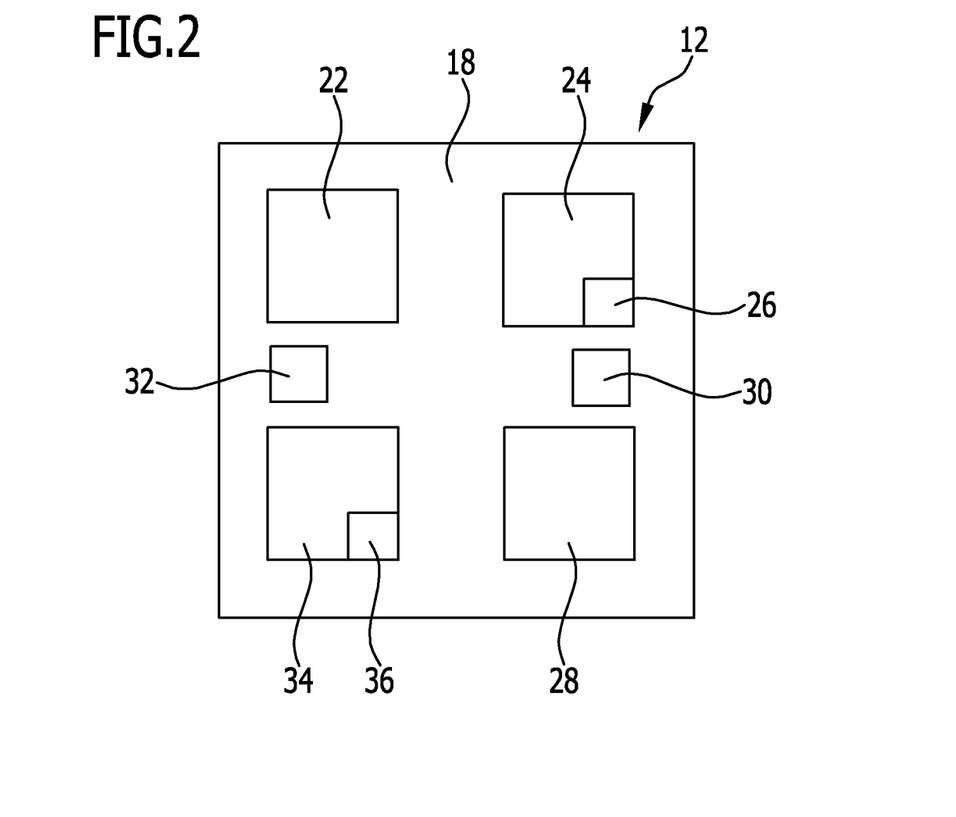
FIG. 2: a schematic block diagram of the navigation system from FIG. 1.

The navigation system 12, see also FIG. 2, is a hand-held, integrated navigation system. As used herein, "integrated" is, in particular, to be understood as meaning that all of the components of the navigation system 12 are arranged in a common housing 18. The navigation system 12 is configured, in particular, as tablet computer or, in the present case, as smartphone 20. The smartphone 20 can be operated in a user-friendly way by a surgeon and preferably moved freely in space.

The navigation system 12 comprises a data processing unit 22 which, for example, comprises a microprocessor or is configured as such. A data processing program, with which optical images of a detection unit 24 of the navigation system 12 can be analyzed, is executable by the data processing unit 22. Accordingly, the data processing program comprises, in particular, image processing algorithms. The detection unit 24 comprises one and preferably precisely one digital camera 26.

In addition to the detection unit 24, the data processing unit 22 is also in electrical connection with a display unit 28, a sensor unit 30 and a communication interface 32 of the navigation system 12.

The display unit 28 is configured, in particular, as touch screen.

The sensor unit 30 comprises an inclination sensor, with which an inclination of the navigation system 12 in several directions in space is determinable in an absolute reference system, specifically a world coordinate system. It is thereby possible, for example, to determine the inclination of the navigation system 12 relative to the horizontal plane.

Via the communication interface 32, data can be transmitted by the navigation system 12 to an external, spatially separate receiver. It is preferably a wireless communication interface 32. The data may include, in particular, images of the camera 26 and also location and/or orientation data of medical marking devices, characteristic points referenced by these, reference points or anatomical landmarks.

The navigation system 12 further comprises an illumination unit 34 for at least partially illuminating a field of view of the camera 26. The illumination unit 34 preferably comprises at least one LED light source 36. Expediently, the illumination unit 34 emits light in the visible spectral range of approximately 400 nm to approximately 800 nm or part thereof.

The instrumentation 10 comprises at least one medical marking device 38. The marking device 38 may be a component of the fixation system 14. In the present case, two marking devices 38, 40 are provided. The marking devices 38 and 40 are functionally identical, but are different in spatial configuration. This makes it possible for both marking devices 38, 40 to be detected, identified and tracked in space with respect to location and/or orientation separately or simultaneously with the navigation system 12.

Figure 3:
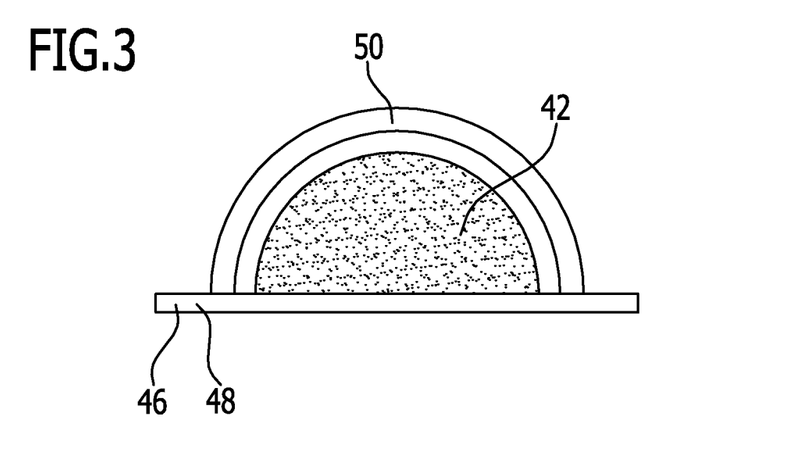
FIG. 3: a schematic partial illustration of a marking element of a medical marking device.

The marking devices 38, 40 each comprise a plurality of medical marking elements 42, partly illustrated schematically in FIG. 3. The marking elements 42 are fixed on a holding element 44. The marking elements 42 are designed to reflect the light emitted by the LED light source 36. In this way, signal components of the marking elements 42 can be reliably detected by the camera 26 and reliably identified by the data processing unit 22.

To increase the contrast between the marking elements 42 and the holding element 44, the marking devices 38, 40 comprise respective contrast enhancement elements 46. The contrast enhancement elements 46 are configured as the rings 48. The reflectivity of the rings 48 for the light emitted by the LED light source 36 is lower than the reflectivity of the marking elements 42.

The rings 48 surround the marking elements 42 and a respective protective element 50 associated with these. The protective elements 50 are spherical cap-shaped and surround the marking elements 42. The protective elements 50, therefore, have a hood-shaped configuration. They are transparent for the light emitted by the LED light source 36 and protect the marking elements 42 against soiling, for example, by blood.

The fixation system 14 serves to stabilize the vertebrae 16 relative to one another. For this purpose, the fixation system 14 comprises in a manner known per se anchoring elements in the form of bone screws 52. The bone screws 52 can be fixed in the respective vertebrae 16. Furthermore, the navigation system 12 comprises a connecting element (FIG. 8) in the form of a rod 54. The rod 54 can be fixed in a clamping manner to the bone screws.

The fixation system 14 further comprises extension elements in the form of extension tubes 56. The extension tubes 56 can be connected in a manner known per se with force-locking and/or positive locking to the bone screws 52. The bone screws 52 can preferably be acted upon percutaneously.

The marking devices 38, 40 can be releasably and selectively fixed to the extension tubes 56. An adapter element 58 held on the extension tube 56 is, for example, provided for this purpose.

The geometry of the adapter element 58 and the extension tube 56 is stored in the navigation system 12. By detecting the location and/or orientation of one of the marking devices 38, 40, the location and orientation of the bone screw 52 to which the corresponding extension tube 56 is connected can be concluded therefrom.

The mode of operation and the use of the instrumentation 10, in particular, of the navigation system 12 will be explained hereinbelow.

With the navigation system 12, reference points which are defined by the bone screws 52 are determined in a reference coordinate system. Accordingly, the bone screws 52 are reference elements. The reference coordinate system is defined by one of the marking devices 38, 40, in the present case, for example, by the marking device 38.

The surgeon takes an image of the operating site which includes, in particular, the marking devices 38, 40 (FIG. 1) with the camera 26 of the navigation system 12. The marking device 38 is coupled to one of the bone screws 52, the marking device 40 to the bone screw lying beside it.

In the image of the camera 26, the marking elements 42 can be reliably recognized owing to their reflecting characteristic and the illumination by means of the LED light source 36 and the location and the orientation of the marking devices 38, 40 thereby determined by the data processing unit 22 by means of image processing algorithms. This makes it possible to determine a space vector of the reference points defined by the bone screws 52 in the reference coordinate system.

It is particularly advantageous that by taking into consideration a signal of the sensor unit 30 it can be determined how the orientation of the space vector runs in the absolute coordinate system. This is possible without a priori knowledge of the position and orientation of the patient and without the patient having to be fixed for this.

Figure 5:
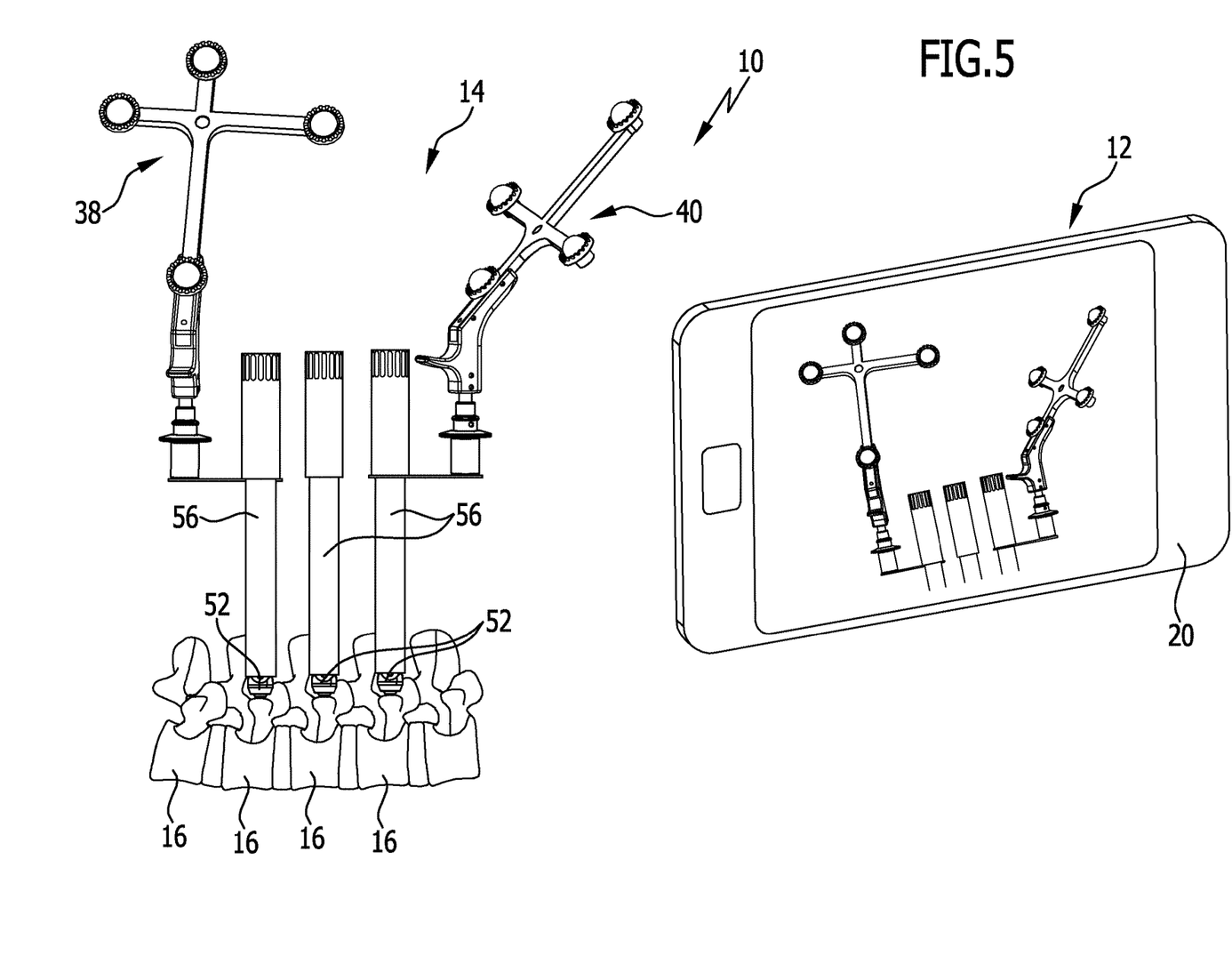
FIG. 5: a further illustration of the instrumentation from FIG. 1.

In the further course of the operation, the marking device 40 can be connected to a further extension tube 56. The further extension tube 56 is coupled to the next one of the bone screws 52 (FIG. 5). The marking device 38 remains coupled to the first bone screw 52. The reference coordinate system continues to be defined by the marking device 38, and the location of the further bone screw 52 which is now referenced by the marking device 40 can also be determined in the reference coordinate system.

A further image of the operating site, which includes the marking devices 38 and 40, is taken with the camera 26. It is also conceivable for not individual images but an image sequence in the form of a video to be taken. With the further image or images, the further space vector between the reference points as defined by the bone screws 52 can be determined in the reference coordinate system.

Figure 6:
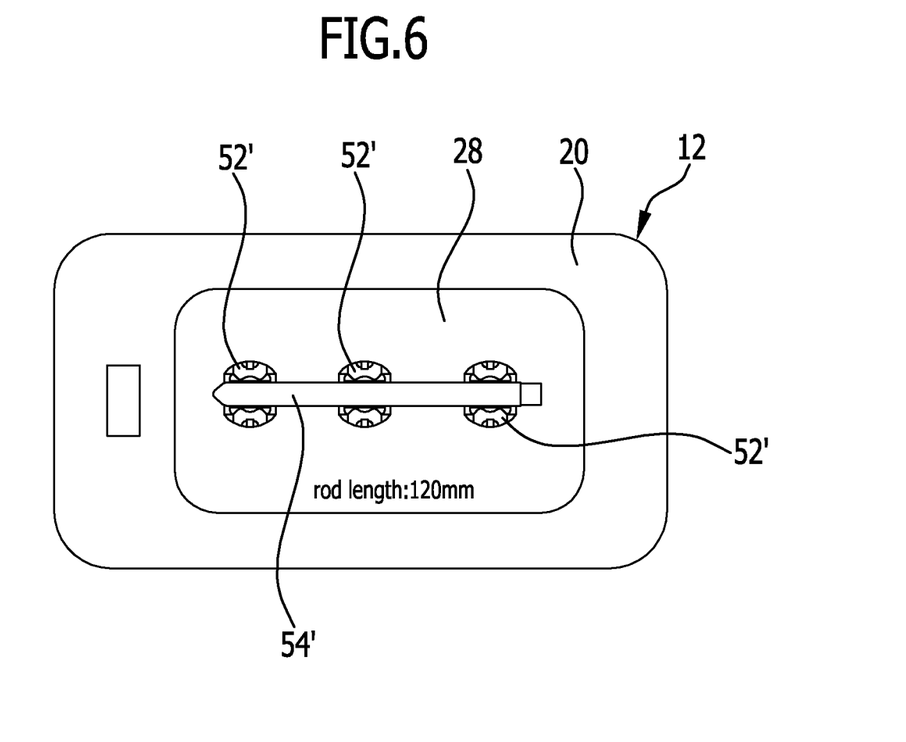
FIG. 6: a schematic illustration of the navigation system from FIG. 1 with an indication displayed by it for selection of a connecting element.
Figure 7:
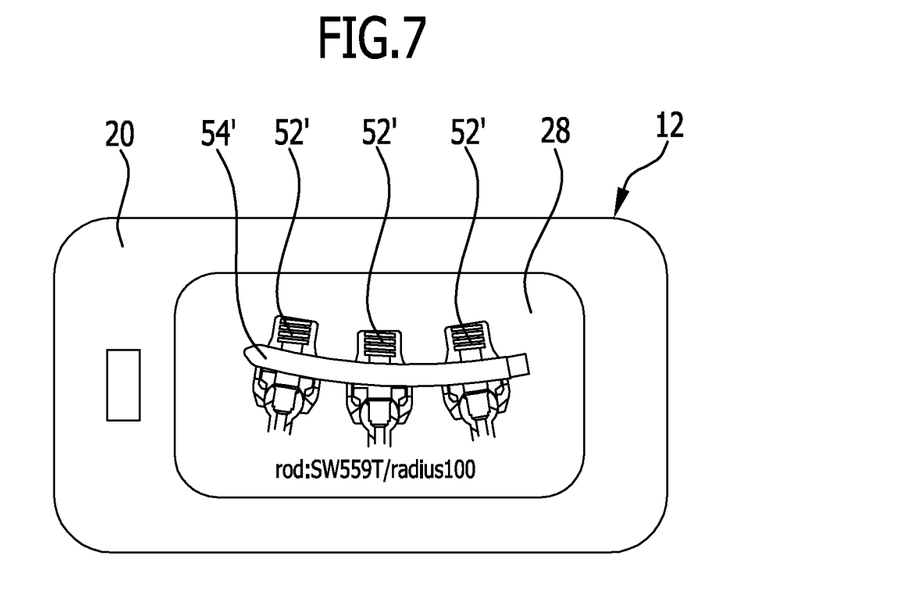
FIG. 7: a further illustration corresponding to FIG. 6.

From the space vectors, a (in the present case, an open) polygonal line of the reference points can be calculated in the reference coordinate system. On the basis of this information, the data processing unit 42 can offer the surgeon on the display unit 28 a proposal for a rod 54 to be used, with which the bone screws 52 can be fixed in the desired relative orientation. FIGS. 6 and 7 show, by way of example, the length of the proposed rod 54 and its type and its rod curvature, respectively.

Figure 8:
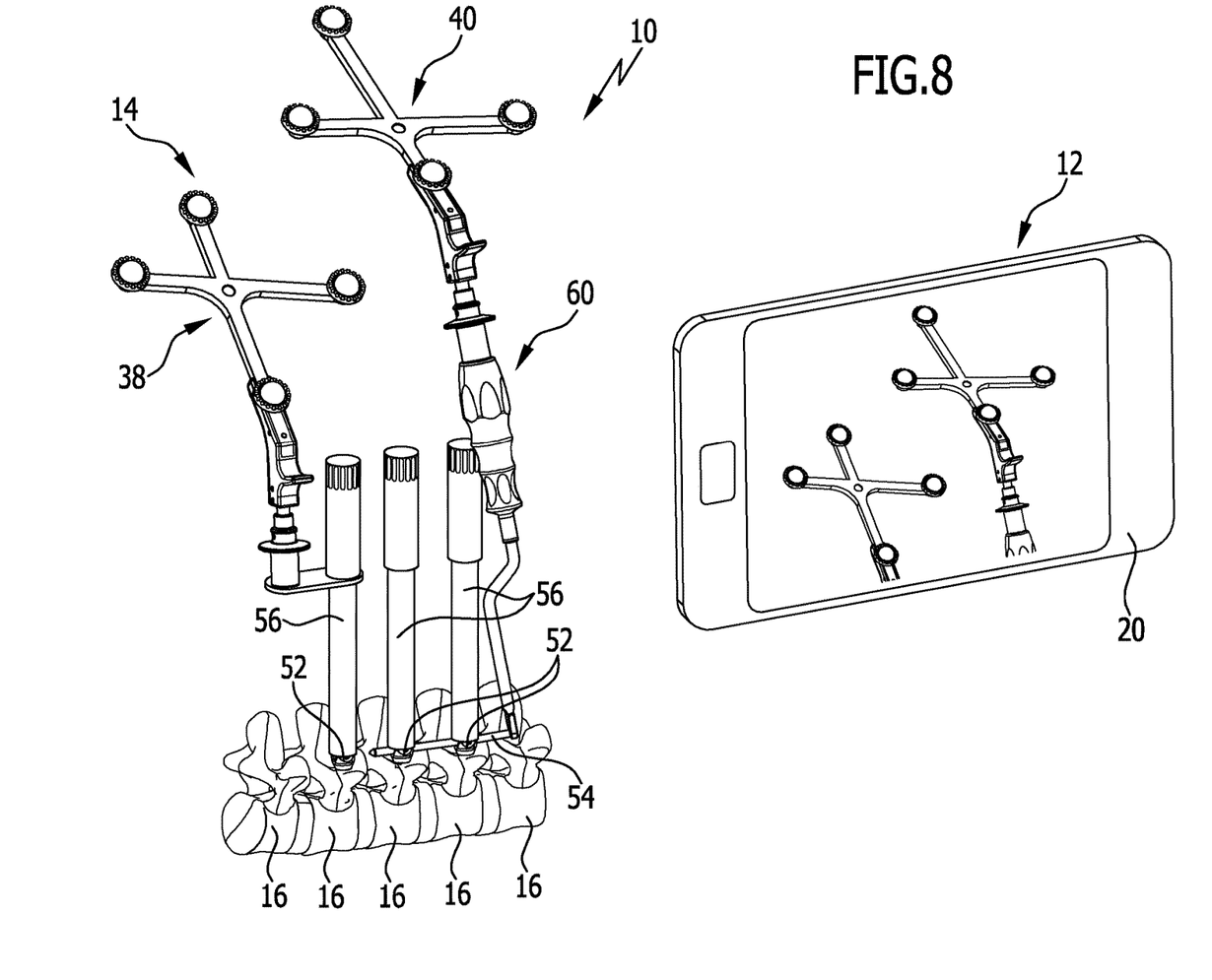
FIG. 8: the instrumentation from FIG. 1 when inserting the connecting element.
Figure 9:
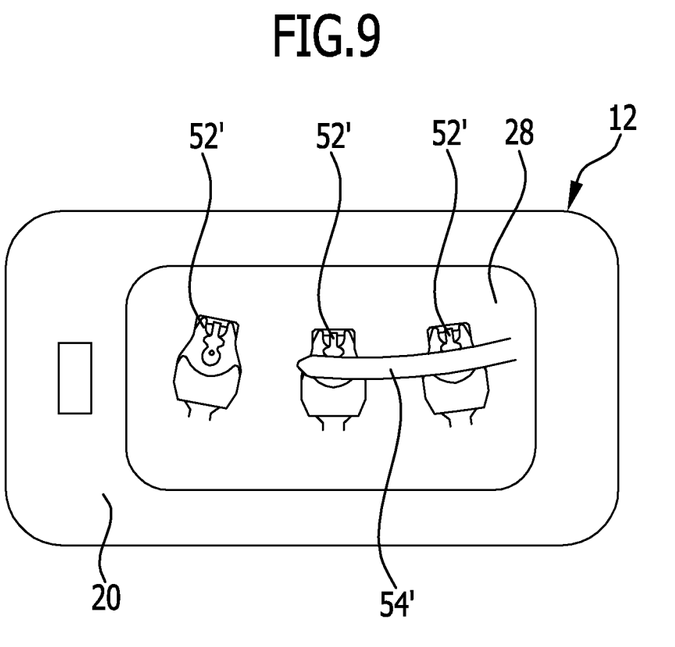
FIG. 9: a schematic illustration of the navigation system giving an indication for insertion of the connecting element.
Figure 10:
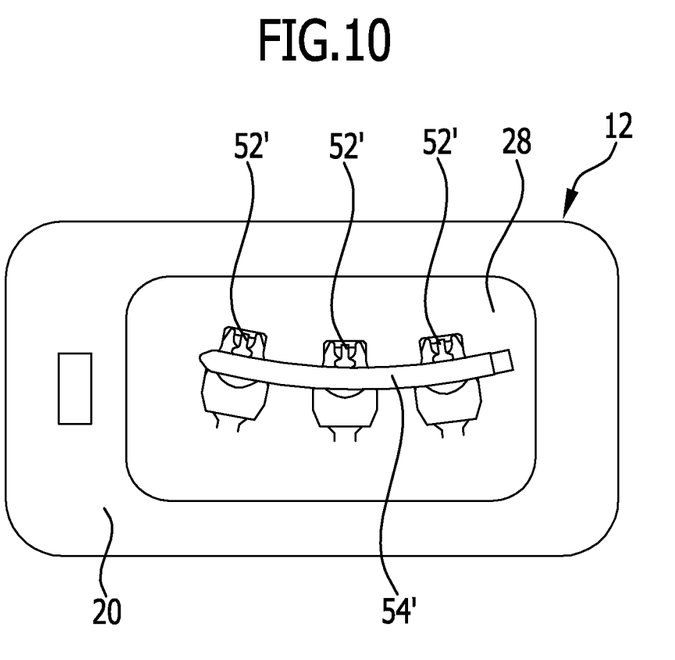
FIG. 10: a further illustration corresponding to FIG. 9.

The navigation system 12 can also be used to assist the implantation of the rod 54 (FIGS. 8 to 10). For implantation of the rod 54, it is fixed to an insertion or implantation tool 60. A marking device, in the present case, the marking device 40, is connected to the implantation tool 60. Owing to the known geometry of the implantation tool 60 and the rod 54, the location and orientation of the rod 54 can be determined in the reference coordinate system. The reference coordinate system continues to be defined by the marking device 38 which remains fixed to the first of the extension tubes 56 and to the first bone screw 52.

With the camera 26 the user creates further images or image sequences of the operating site in which the marking devices 38 and 40 are captured. The data processing unit 22 can determine the location and orientation of the rod 54 relative to the bone screws 52 by means of image processing. The operator can be given instructions via the display unit 28 for guiding the implantation tool 60. FIGS. 9 and 10 show this schematically. Symbols of the rod 54 and the bone screws 52 can be inserted on the display unit 28. On the basis of these symbols, the user can guide the implantation tool 60 in such a way that the rod 54 is led through insertion openings arranged on the bone screws 52. The instructions can be inserted instead of the image created by the camera 26 or superimpose it.

The symbols of the bone screws 52 and the rod 54 on the display unit 28 are designated by the same reference numeral and an additional prime mark (') in the drawings.

As mentioned above, information recorded during the operation such as reference points, anatomical landmarks or, in particular, also images of the camera 26 can be transmitted to an external receiver via the communication interface 32. This can be used, for example, to document the operation or for training purposes.

Figure 4:
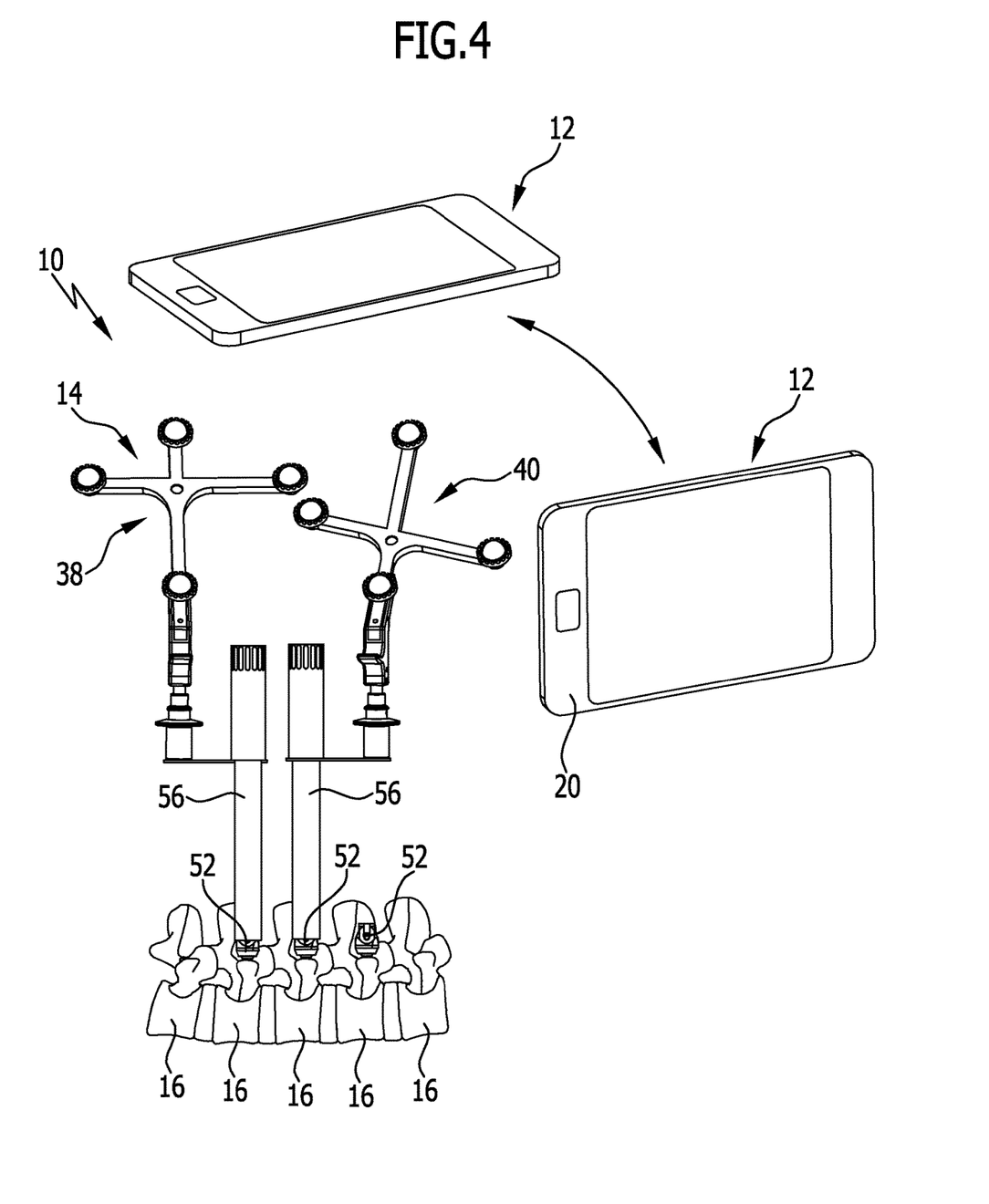
FIG. 4: the instrumentation from FIG. 1 in a further illustration.

With the instrumentation 10, it proves particularly expedient that the navigation system 12 is integrated and hand-held and free of any fixation in space. This enables the surgeon to move the navigation system 12 freely in space so as to take as good images of the operating site as possible. This is illustrated, by way of example, in FIG. 4 which shows the navigation system 12 in two different orientations relative to the fixation system 14.

LIST OF REFERENCE NUMERALS 10 instrumentation
12 navigation system
14 fixation system
16 vertebra
18 housing
20 smartphone
22 data processing unit
24 detection unit
26 camera
28 display unit
30 sensor unit
32 communication interface
34 illumination unit
36 LED light source
38 marking device
40 marking device
42 marking element
44 holding element
46 contrast enhancement element 48 ring
50 protective element
52 bone screw
54 rod
56 extension tube
58 adapter element
60 implantation tool

What is claimed is:

1. Medical instrumentation, comprising:
    a hand-held, integrated, medical navigation system which comprises:
        a housing,
        an optical detection unit having a camera disposed in the housing,
        a data processing unit disposed in the housing,
        an optical display unit disposed in the housing,
        the data processing unit being coupled to the detection unit and the display unit, it being possible for location and orientation data of a medical marking device which is detectable with the detection unit to be processed by the data processing unit, and information relating thereto to be represented on the display unit,
        a sensor unit disposed in the housing for providing a signal relating to the inclination of the navigation system in at least one direction in space of an absolute reference system, and
        an illumination unit disposed on or in the housing with which light is emittable in a direction of the marking device detectable with the detection unit,
    two or more reference elements to be referenced,
    two or more medical marking devices, each of the two or more medical marking devices comprising a plurality of marking elements which are configured for retroflection of the light of the illumination unit,
    the data processing unit being configured to:
    determine a respective space vector between reference points referenced by the two or more medical marking devices, with one of the two or more medical marking devices being usable as a reference marking device for defining a reference coordinate system,
    determine an orientation of the space vector in the absolute reference system based on a signal of the sensor unit, and
    on the basis of the orientations of two or more of the space vectors, defining a plane in the reference coordinate system, and determine an inclination of the plane relative to the reference plane, in the absolute reference system,
    wherein:
    the two or more medical marking devices are adapted for selective coupling to the reference elements,
    a relative position of the reference elements is determinable by means of the data processing unit in the reference coordinate system,
    the reference elements are or comprise bone screws, and
    the two or more medical marking devices with extension elements are adapted for coupling percutaneously to the bone screws.

2. Instrumentation in accordance with claim 1, wherein the navigation system is configured as smartphone or as tablet computer.

3. Instrumentation in accordance with claim 1, wherein the illumination unit comprises at least one LED light source.

4. Instrumentation in accordance with claim 1, wherein visible light is emittable by the illumination unit.

5. Instrumentation in accordance with claim 1, wherein the detection unit comprises precisely one camera.

6. Instrumentation in accordance with claim 1, wherein an image recordable with the camera is representable on the display unit.

7. Instrumentation in accordance with claim 1, wherein the navigation system further comprises a communication interface for transmitting data to an external receiving unit.

8. Instrumentation in accordance with claim 1, wherein the navigation system is freely movable in space and is free of any mechanical coupling with a surgical instrument or an implant.

9. Instrumentation in accordance with claim 1, wherein:
    the two or more medical marking devices each comprise a holding element on which the marking elements are held, and contrast enhancement elements, a respective contrast enhancement element being associated with the marking elements in order to increase the contrast between the marking elements and the holding element, and/or
    the two or more medical marking devices each comprise hood-shaped protective elements which are associated with a respective marking element and which are transparent for the light emitted by the illumination unit.

10. Instrumentation in accordance with claim 1, wherein the two or more medical marking devices are simultaneously detectable with the detection unit, and the space vector is determinable with the data processing unit on the basis of an image of the camera.

11. Instrumentation in accordance with claim 1, wherein:
    the instrumentation further comprises a connecting element for connecting the reference elements, and
    a geometry of the connecting element is determinable by the data processing unit in order to connect the reference elements.

12. Instrumentation in accordance with claim 11, wherein the connecting element is adapted for coupling to one of the two or more medical marking devices, and the position of the connecting element relative to the reference elements is determinable by the data processing unit and indications are providable for a user on the display unit for guiding the connecting element.

13. Instrumentation in accordance with claim 11, wherein:
    the connecting element is a rod, and
    the one of the two or more medical marking devices is fixed or fixable to an insertion or implantation tool for guiding the rod.

14. Medical instrumentation, comprising:
    a hand-held, integrated, medical navigation system which comprises:
        a housing,
        an optical detection unit having a camera disposed in the housing,
        a data processing unit disposed in the housing,
        an optical display unit disposed in the housing,
        the data processing unit being coupled to the detection unit and the display unit, it being possible for location and orientation data of a medical marking device which is detectable with the detection unit to be processed by the data processing unit, and information relating thereto to be represented on the display unit,
        a sensor unit disposed in the housing for providing a signal relating to the inclination of the navigation system in at least one direction in space of an absolute reference system, and an illumination unit disposed on or in the housing with which light is emittable in a direction of the marking device detectable with the detection unit, two or more reference elements to be referenced, a connecting element for connecting the reference elements, two or more medical marking devices, each of the two or more medical marking devices comprising a plurality of marking elements which are configured for retroflection of the light of the illumination unit, the data processing unit being configured to:

determine a respective space vector between reference points referenced by the two or more medical marking devices, with one of the two or more medical marking devices being usable as a reference marking device for defining a reference coordinate system, determine an orientation of the space vector in the absolute reference system based on a signal of the sensor unit, and on the basis of the orientations of two or more of the space vectors, defining a plane in the reference coordinate system, and determine an inclination of the plane relative to the reference plane, in the absolute reference system, wherein:

the two or more medical marking devices are adapted for selective coupling to the reference elements, a relative position of the reference elements being determinable by means of the data processing unit in the reference coordinate system, and a geometry of the connecting element is determinable by the data processing unit in order to connect the reference elements.

15. Instrumentation in accordance with claim 14, wherein:

the reference elements are or comprise bone screws, and the two or more medical marking devices with extension elements are adapted for coupling percutaneously to the bone screws.

16. Instrumentation in accordance with claim 14, wherein the connecting element is adapted for coupling to one of the two or more medical marking devices, and the position of the connecting element relative to the reference elements is determinable by the data processing unit and indications are providable for a user on the display unit for guiding the connecting element.

17. Instrumentation in accordance with claim 14, wherein:

the connecting element is a rod, and the one of the two or more medical marking devices is fixed or fixable to an insertion or implantation tool for guiding the rod.

* * * * *